(12) United States Patent
Park et al.

(10) Patent No.: US 11,865,133 B2
(45) Date of Patent: Jan. 9, 2024

(54) PHARMACEUTICAL COMPOSITION COMPRISING ORGANOID AND ANTI-INFLAMMATORY AGENT FOR PREVENTING OR TREATING INFLAMMATORY BOWEL DISEASE

(71) Applicant: ORGANOIDSCIENCES LTD., Daejeon (KR)

(72) Inventors: Jun-Hyeok Park, Seongnam-si (KR); Hyemi Jeon, Seongnam-si (KR); Taegyu Lim, Seongnam-si (KR); Hayoung Song, Seongnam-si (KR); Han Kyung Kim, Seongnam-si (KR); Hyokyung Lee, Seongnam-si (KR); Ji Hye Tak, Seongnam-si (KR)

(73) Assignee: ORGANOIDSCIENCES LTD., Daejeon (KR)

( * ) Notice: Subject to any disclaimer, the term of this patent is extended or adjusted under 35 U.S.C. 154(b) by 71 days.

(21) Appl. No.: 18/013,770

(22) PCT Filed: Sep. 16, 2022

(86) PCT No.: PCT/KR2022/013907
§ 371 (c)(1),
(2) Date: Dec. 29, 2022

(87) PCT Pub. No.: WO2023/043272
PCT Pub. Date: Mar. 23, 2023

(65) Prior Publication Data
US 2023/0210886 A1    Jul. 6, 2023

(30) Foreign Application Priority Data

Sep. 17, 2021    (KR) .................. 10-2021-0124721

(51) Int. Cl.
*A61K 31/7125* (2006.01)
*A61P 1/04* (2006.01)
*A61K 31/713* (2006.01)

(52) U.S. Cl.
CPC ........ *A61K 31/7125* (2013.01); *A61K 31/713* (2013.01); *A61P 1/04* (2018.01)

(58) Field of Classification Search
CPC .. A61P 43/00; A61P 1/00; A61P 29/00; A61P 35/00; A61P 37/00; A61P 11/00; A61P 21/00; A61P 9/00; A61P 1/16; A61P 25/28; A61P 27/02; A61P 1/04; A61P 25/00; A61P 3/00; A61P 25/16; A61P 3/06; A61P 37/02; A61P 13/12; A61P 19/08; A61P 19/10; A61P 25/14; A61P 25/18; A61P 31/12; A61P 31/14; A61P 31/18; A61P 35/02; A61P 7/00; A61P 37/06; A61P 1/06; A61P 17/00; A61P 31/04; A61P 1/12; A61P 3/10; A61P 1/14; A61P 13/00; A61P 19/00; A61P 25/04;
A61P 29/02; A61P 3/04; A61P 31/00; A61P 33/00; A61P 37/08; A61K 35/742; A61K 9/0053; A61K 2035/115; A61K 35/39; A61K 35/74; A61K 35/741; A61K 45/06; A61K 35/744; A61K 35/745; A61K 35/747; A61K 31/7004; A61K 31/7016; A61K 31/715; A61K 38/46; A61K 9/0031; A61K 9/19; A61K 48/005; A61K 48/0058; A61K 49/0019; A61K 49/0026; A61K 49/0028; A61K 49/0058; A61K 49/0069; A61K 2300/00; A61K 48/00; A61K 38/465; A61K 48/0091; A61K 31/19; A61K 35/17; A61K 35/28; A61K 38/00; A61K 38/18; A61K 38/20; A61K 39/3955; A61K 9/0048; A61K 9/0056; A61K 9/1271; A61K 9/5184; A61K 2035/124; A61K 2039/505; A61K 35/30; A61K 35/37; A61K 35/38; A61K 38/1709; A61K 38/179; A61K 47/26; A61K 9/28; A61K 9/50; A61K 2035/128; A61K 31/06; A61K 31/155; A61K 31/17; A61K 31/255; A61K 31/426; A61K 31/5575; A61K 31/675; A61K 31/706; A61K 31/7088; A61K 31/7105; A61K 35/12; A61K 35/13; A61K 35/33; A61K 35/34; A61K 36/074; A61K 38/16; A61K 38/1793; A61K 38/21; A61K 38/217; A61K 47/10; A61K 47/28;
(Continued)

(56) References Cited

FOREIGN PATENT DOCUMENTS

KR    10-2017-0113081 A    10/2017

OTHER PUBLICATIONS

Written Decision on Registration (Decision to Grant Patent) dated Aug. 24, 2022 for related Korean Patent Application No. 10-2021-0124721.

(Continued)

*Primary Examiner* — Audrea B Coniglio
(74) *Attorney, Agent, or Firm* — Sughrue Mion, PLLC

(57) ABSTRACT

The present disclosure relates to a pharmaceutical composition for preventing or treating inflammatory bowel disease, comprising an intestinal organoid and a TNFα inhibitor. The combination use of the intestinal organoid and TNFα inhibitor according to the present disclosure can alleviate symptoms of inflammatory bowel disease such as weight loss, diarrhea, and bloody stool, and can inhibit fibrosis of the intestinal mucosa due to inflammation. In particular, when the intestinal organoid and the anti-inflammatory TNFα inhibitor are used in combination, the therapeutic effect is significantly superior to that of multiple administrations of the TNFα inhibitor, and thus it can be usefully used as an agent for preventing or treating inflammatory bowel disease.

7 Claims, 11 Drawing Sheets

(58) Field of Classification Search
CPC ............ A61K 48/0041; A61K 48/0066; A61K 49/0032; A61K 49/0043; A61K 49/0056; A61K 9/0014; A61K 9/0073; A61K 9/0097; A61K 9/127; A61K 9/1272; A61K 9/16

See application file for complete search history.

(56) References Cited

OTHER PUBLICATIONS

Request for Submission of an Opinion dated Apr. 7, 2022 for related Korean Patent Application No. 10-2021-0124721.

PHARMACEUTICAL COMPOSITION COMPRISING ORGANOID AND ANTI-INFLAMMATORY AGENT FOR PREVENTING OR TREATING INFLAMMATORY BOWEL DISEASE

This Application is a National Stage of International Application No. PCT/KR2022/013907 filed Sep. 16, 2022, claiming priority based on Korean Patent Application No. 10-2021-0124721 filed Sep. 17, 2021, the entire disclosures of which are incorporated herein by reference.

TECHNICAL FIELD

The present disclosure relates to a pharmaceutical composition for preventing or treating an inflammatory bowel disease, comprising an intestinal organoid and a TNFα inhibitor.

BACKGROUND ART

An inflammatory bowel disease is a chronic disease in which the occurrence and recovery of inflammation is repeated in various parts of the intestine, such as the large intestine and rectum. Recurrence is common, and symptoms such as chronic diarrhea, abdominal pain, bloody stool and weight loss occur. In addition, fibrosis of the intestinal mucosa is progressed by inflammation. When the intestinal fibrosis occurs, the length of the intestine is shortened and hardened, and such changed intestinal tissue delays the absorption of nutrients. In severe cases, an intestinal stenosis may occur.

Currently, treatment of inflammatory bowel disease is mainly aimed at reducing inflammation and improving symptoms such as bloody stool and diarrhea Immunomodulators, anti-inflammatory agents, steroids, etc. are used as drugs for inflammatory bowel disease. For example, for treating Crohn's disease, an anti-inflammatory agent or a steroid is used in a multi-administered form. However, since the inflammatory bowel disease is a chronic intractable disease whose cause is not clear, the drug treatment often does not improve symptoms. Also, since main treatment mechanism of the drug is to reduce inflammation rather than fundamental treatment, continuous drug administration and reduced immunity may cause an infection. Therefore, a surgery is performed when the drug treatment is not effective or complications such as stenosis, perforation, and colon cancer occur. For example, surgery is performed to remove an inflamed part for Crohn's disease and a part of large intestine for ulcerative colitis. In the case of surgery, the effect of treatment is high in that it completely removes the inflamed area, but there is a problem with the inconvenience of daily life.

Accordingly, the development of drugs for fundamentally treating inflammatory bowel disease is being actively studied. As an example, a treatment method for regenerating tissue damaged due to repeated inflammations using a biological agent such as stem cells has been studied. However, in the case of stem cell therapeutics, it has been reported in the results of clinical trials administering stem cells that the degree of improvement of the damaged tissue is not significant, or the improvement effect does not last for a long time. In addition, as a result of long-term follow-up, it was pointed out as a limitation that the rate of long-term survival of transplanted adult stem cells is extremely low in vivo after transplantation. There is an urgent need to develop a therapeutic agent that enhances the efficacy of a biological agent used for the treatment of inflammatory bowel disease and further lowers the recurrence rate.

Technical Problem

The inventors have conducted various studies on a method for treating inflammatory bowel disease without relapse by improving the disadvantages of drugs previously used for the treatment of inflammatory bowel disease. As a result, when the intestinal organoid and the anti-inflammatory TNFα inhibitor are used in combination, it shows a synergistic effect in the treatment of weight loss, diarrhea, bloody stool, intestinal fibrosis, etc. compared to using those alone. In particular, the present invention has been completed by experimentally demonstrating that it can exhibit a remarkably excellent therapeutic effect compared to administering TNFα inhibitor multiple times.

Technical Solution

One aspect of the present disclosure provides a pharmaceutical composition comprising an intestinal organoid and a TNFα inhibitor for preventing or treating inflammatory bowel disease.

The term "organoid" as used herein refers to a cell mass having a three-dimensional structure and refers to an organ mimic prepared through three-dimensional culture of cells isolated from tissues or organs. Organoid can reproduce the particular function and shape of the human tissue or organ because it comprises specific cell populations constituting tissues or organs and is structurally organized in a form similar to actual tissues or organs of human body.

The term "intestinal organoid" as used herein refers to an organoid derived from a cell isolated from an intestine. Specifically, the intestine includes small intestine, large intestine, colon, rectum and caecum, and the intestinal organoid includes a small intestine organoid, a large intestine organoid, a colon organoid, a rectum organoid, and a caecum organoid.

The term "TNFα" as used herein refers to cytokine called tumor necrosis factor-α. Specifically, the TNFα inhibitor includes a compound, a protein, a fusion protein, a compound-protein complex, a drug-protein complex, an antibody, a compound-antibody complex, a drug-antibody complex, an amino acid, a peptide, a virus, a carbohydrate, a lipid, a nucleic acid, an extract, and a fraction, but is not limited thereto. As used herein, "inhibitor" may be used interchangeably with "suppressor" or "antagonist", and "inhibition" may also be used interchangeably with "suppression".

The TNFα inhibitor includes, for example, a compound, a peptide, a peptide mimetic, a fusion protein, an antibody, an aptamer, or an antibody-drug conjugate (ADC) that binds specifically to the TNFα protein, but is not limited thereto.

The term "specific" or "specifically" refers to the ability to bind to only a target protein without affecting other proteins in the cell.

The term "antibody" includes a monoclonal antibody, a polyclonal antibody, a bispecific antibody, a multispecific antibody, a chimera antibody, a humanized antibody and a human antibody, and also includes new antibodies as well as antibodies known to the art or commercialized in the art. The antibody includes not only the forms having a full length comprising two heavy chains and two light chains but also the functional fragments of antibody molecules, so long as it specifically binds to TNFα protein. The functional fragment of antibody molecule refers to a fragment at least having its antigen-binding function, and may include Fab, F(ab'), F(ab')$_2$, Fv, etc., but is not limited thereto. The term "peptide mimetic" refers to a peptide or a non-peptide which inhibits the protein binding domain that induces an activation of TNFα. The term "aptamer" refers to a single strand nucleic acid (such as DNA, RNA or modified nucleic acid) having in itself a stable tertiary structure and being able to bind to a target molecule with high affinity and specificity.

The TNFα inhibitor includes, for example, an antisense nucleic acid, a siRNA, a shRNA, a miRNA or a ribozyme that binds in a complementary manner to a DNA or a mRNA of TNFα, but is not limited thereto.

The term "antisense nucleic acid" refers to DNAs or RNAs comprising nucleic acid sequences complementary to the sequence of particular mRNA, or fragments or derivatives thereof, which bind to or hybridize with the complementary sequences in mRNA and inhibit the translation of mRNA into protein. The term "siRNA (small interfering RNA)" refers to a short double chain RNA which is able to induce the RNAi (RNA interference) through cleavage of particular mRNA. The siRNA comprises a sense RNA strand having a sequence homologous to the mRNA of the target gene, and an antisense RNA strand having a sequence complementary thereto. The siRNA can inhibit the expression of the target gene, and thus can be used in gene knockdown, genetic therapy, etc. The term "shRNA (short hairpin RNA)" is a single strand RNA, which comprises a stem portion forming a double strand portion through hydrogen bonds, and a loop portion. It is processed by a protein such as Dicer to be converted into siRNA, and performs the same function as siRNA. The term "miRNA (micro RNA)" refers to a 21 to 23 nt non-coding RNA which modulates gene expression after transcription by promoting the degradation of target RNA or by suppressing its translation. The term "ribozyme" refers to a RNA molecule that has an enzyme-like function, recognizing a particular base sequence and cutting the same. The ribozyme comprises an area that specifically binds to a complementary base sequence of a target messenger RNA strand, and an area that cleaves the target RNA.

The antisense nucleic acid, siRNA, shRNA, miRNA, ribozyme, etc. that binds complementarily to the DNA or mRNA of TNFα can inhibit the transcription of TNFα, its translocation into the cytoplasm, its maturation, its translation, or any other activities crucial for the biological functions of TNFα.

The pharmaceutical composition according to the present disclosure comprising an effective amount of a TNFα inhibitor can be administered to a subject in need of prevention or treatment of inflammatory bowel disease.

The term "prevention" or "preventing" as used herein refers to any action in which inflammatory bowel disease is inhibited or delayed by administration of the composition according to the present disclosure. The term "treatment" or "treating" as used herein refers to any action in which symptoms of inflammatory bowel disease are improved or cured by administration of the composition according to the present disclosure.

The pharmaceutical composition of the present disclosure can prevent or treat the inflammatory bowel disease, for example, radiation colitis, radiation proctitis, ischemic colitis, intestinal Behcet's disease, Crohn's disease, ulcerative colitis and ulcerative proctitis, but is not limited thereto.

The pharmaceutical composition of the present disclosure can decrease DAI (Disease Activity Index).

The term "DAI" as used herein refers to a disease activity index for inflammatory bowel disease, and indicates the severity of symptoms of inflammatory bowel disease such as, specifically, weight loss, stool consistency, and fecal occult blood. The higher DAI means the more severe symptoms of inflammatory bowel disease, and the lower DAI means the less severe symptoms of inflammatory bowel disease. Specifically, DAI of 0 to 1 means normal, DAI of 2 to 4 means mild, DAI of 5 to 7 means severe, and DAI of 8 to 10 means critical. Preferably, the pharmaceutical composition can reduce DAI by 2 to 3 points or more, which means alleviating severe and/or critical inflammatory bowel disease into mild inflammatory bowel disease.

In addition, the pharmaceutical composition of the present disclosure can improve or ameliorate one or more symptoms selected from the group consisting of weight loss, stool consistency and fecal occult blood. The "weight loss" means a symptom in which a body weight of the subject decreases because of poor dietary intake and absorption of nutrients due to inflammatory bowel disease, the "fecal consistency" means a diarrhea symptom, and the "fecal occult blood" means bloody stool symptom.

The pharmaceutical composition of the present disclosure can inhibit or ameliorate fibrosis caused by inflammation. Intestinal mucosa has been fibrous due to inflammation, which results in shortening and hardening of the intestine. Fibrosis causes abnormal changes in the intestinal tissue, interfering with the intake of nutrients, causing side effects such as intestinal stenosis, and thereby being a factor that hinders the cure of the disease. Therefore, suppressing or alleviating the fibrosis of the intestinal mucosa caused by inflammation can prevent recurrence of inflammatory bowel disease and lead to a cure.

The effective amount may be a "therapeutically effective amount" or a "prophylactically effective amount". As used herein, the term "therapeutically effective amount" refers to, when a drug or a therapeutic agent is used alone or in combination with other therapeutic agents, any amount capable of having a decrease in the severity of a disease, an increase in the frequency and duration of the disease symptom-free period, or a prevention of damage or impairment due to the disease. As used herein, the term "prophylactically effective amount" refers to any amount capable of suppressing an occurrence or recurrence of inflammatory bowel disease. The level of effective amount may be determined depending on factors including severity, age, sex, drug activity, drug sensitivity, administration time, administration route and excretion rate, treatment period, concurrent drugs, and other factors well known in the medical field.

As used herein, the term "administration" or "administering" refers to the physical introduction of the composition to a subject using any of various methods and delivery systems known to a person skilled in the art. The route of administration for the pharmaceutical composition of the present disclosure includes, for example, oral routes, or routes of administration by intravenous, intramuscular, subcutaneous, intraperitoneal, spinal or other parenteral routes, such as by injection or infusion, but is not limited thereto. The administrations of the composition of the present disclosure may be, for example, performed once, multiple times, or over one or more extended periods of time.

It may depend on the age, sex, or weight of the subject. Specifically, it may be administered in an amount of 0.1 to 100 mg/kg once to several times a day, or at intervals of several days to several months depending on the symptom of subject. In addition, the dose may be increased or decreased depending on the administration route, disease severity, sex, weight, age, and the like.

The pharmaceutical composition of the present disclosure may further comprise suitable carriers, excipients or diluents commonly used in its preparation. The carriers, excipients or diluents that may be comprised in the composition include, for example, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil, but are not limited thereto.

As used herein, the term "subject" includes a human or any non-human animal which may be a vertebrate, such as a primate, dog, cow, horse, pig, rodent, such as mouse, rat, guinea pig, etc. The "subject" is used interchangeably with "individual" and "patient".

The intestinal organoid and the TNFα inhibitor in the pharmaceutical composition of the present disclosure may be formulated to be administered simultaneously, sequentially or separately. For example, the intestinal organoid and the TNFα inhibitor may be administered simultaneously as one formulation, or may be administered simultaneously, sequentially, or separately as separate formulations. For simultaneous, sequential, or separate administration, the intestinal organoid and the TNFα inhibitor comprised in the composition of the present disclosure may be formulated separately in each container, or together in the same container. In addition, the effective amount, administration time, administration interval, administration route, and treatment period of the intestinal organoid and the TNFα inhibitor contained in the composition of the present disclosure may be the same or different from each other.

The pharmaceutical composition of the present disclosure may be administered in combination with other therapeutic agents. In this case, the composition of the present disclosure and other therapeutic agents may be administered simultaneously, sequentially, or separately. The other therapeutic agents may be a drug such as compound and protein, which has an effect on prevention, treatment, or improvement of inflammatory bowel disease, but is not limited thereto.

The composition of the present disclosure and other therapeutic agents may be formulated for simultaneous, sequential, or separate administration. For example, the intestinal organoid and the TNFα inhibitor, and other therapeutic agents may be administered simultaneously as one formulation, or may be administered simultaneously, sequentially, or separately as separate formulations. For simultaneous, sequential, or separate administration, the intestinal organoid and the TNFα inhibitor contained in the composition of the present disclosure and other therapeutic agents may be formulated separately in each container, or may be formulated together in the same container. In addition, the effective amount, administration time, administration interval, administration route, and treatment period of the intestinal organoid and the TNFα inhibitor contained in the composition of the present disclosure and other therapeutic agents may be the same or different from each other.

Another aspect of the present disclosure is to provide a method of treating or preventing inflammatory bowel disease in a subject, comprising administering to the subject an intestinal organoid and a TNFα inhibitor.

In the method for preventing or treating inflammatory bowel disease according to the present disclosure, each term has the same meaning as described in the pharmaceutical composition for preventing or treating inflammatory bowel disease, unless otherwise specified.

And also, in the method for preventing or treating inflammatory bowel disease according to the present disclosure, the intestinal organoid and the TNFα inhibitor may be administered sequentially, simultaneously, or separately.

In addition, the intestinal organoid and the TNFα inhibitor may be administered sequentially, simultaneously, or separately with other therapeutic agents.

The "simultaneous" administration means that the intestinal organoid and the TNFα inhibitor are administered at one time through the same formulation, or the intestinal organoid and the TNFα inhibitor, and other therapeutic agents are administered at one time through the same formulation. And also, it means that the intestinal organoid and the TNFα inhibitor are administered at one time through separate formulation, or the intestinal organoid and the TNFα inhibitor, and other therapeutic agents are administered at one time through separate formulation, wherein the route of administration of the intestinal organoid, the TNFα inhibitor and/or the other therapeutic agents may be different from each other.

The "sequential" administration means that the intestinal organoid and the TNFα inhibitor are administered relatively continuously, or the intestinal organoid and the TNFα inhibitor; and other therapeutic agents are administered relatively continuously, allowing the minimum possible time as the time consumed in the administration interval.

The "individual" administration means that the intestinal organoid and the TNFα inhibitor are administered at regular intervals, or the intestinal organoid and the TNFα inhibitor and other therapeutic agents are administered at regular intervals. The administration method of the intestinal organoid, the TNFα inhibitor and/or the other therapeutic agents may be appropriately selected by those skilled in the art considering therapeutic effects and side effects of the patient.

The combination use of the intestinal organoid and TNFα inhibitor according to the present disclosure can alleviate symptoms of inflammatory bowel disease such as weight loss, diarrhea, and bloody stool, and can inhibit fibrosis of the intestinal mucosa due to inflammation. In particular, when the intestinal organoid and the anti-inflammatory TNFα inhibitor are used in combination, the therapeutic effect is significantly superior to that of multiple administrations of the TNFα inhibitor, and thus it can be usefully used as an agent for preventing or treating inflammatory bowel disease.

EXAMPLES

Figure 1:
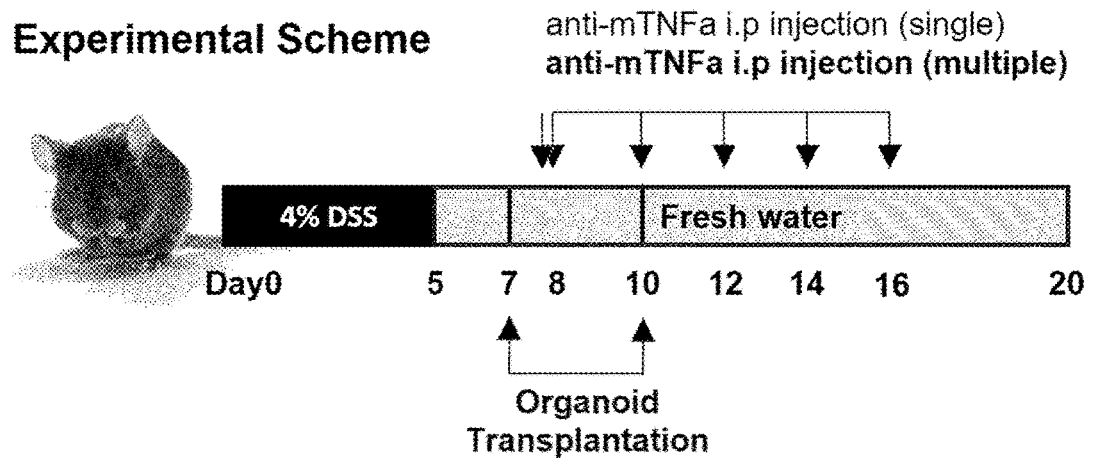
FIG. 1 is a schematic diagram of a method for inducing inflammatory bowel disease using DSS, transplanting an intestinal organoid and administering a TNFα inhibitor.

Hereinafter, the present disclosure will be described in more detail by Examples. However, these examples are only for illustrative purposes, and the scope of the present disclosure is not limited thereto.

Example 1. Effects on DSS-Induced Inflammatory Bowel Disease

Example 1-1. Combination and Transplantation

First, intestinal organoids were transplanted into an inflammatory bowel disease mouse model, and an anti-inflammatory agent was administered to confirm the prevention or treatment efficacy of inflammatory bowel disease by the combination of the intestinal organoid and anti-inflammatory agent.

Specifically, the inflammatory bowel disease mouse model was prepared by feeding C57BL/6 mice (male, 10 weeks, average body weight 24 g) a drinking water with 4 v/v % DSS (dextran sulfate sodium) for 5 days, and then changing to a normal drinking water. When DSS mixed with a drinking water was orally administered, an acute colitis with edema, redness, ulcer and bloody stool was induced throughout the whole intestine, and infiltration of neutrophils into the tissues is observed. As time passes, lymphocytes were infiltrated and chronic inflammation was showed.

Then, a total of 2 transplants of GFP-expressing mouse intestinal organoids were performed at a number of $5 \times 10^5$ cells/animal on the 7th day (day 7) and the 10th day (day 10) from the start of the experiment. Transplantation was carried out by an endoscopic transplantation method, wherein an intestinal organoid in the form of a clump mixed with 50 μl of fibrinogen was administered first, and 50 μl of thrombin was administered secondarily. A TNFα inhibitor was used as an anti-inflammatory agent, and 100 μl of an anti-mouse TNFα antibody (5 mg/kg, BioLegend) was intraperitoneally injected. At this time, single administration was performed on the 8th day (day 8), one day after the transplantation on the 7th day. In the case of multiple administration, a total of 5 administrations (day 8, day 10, day 12, day 14, day 16) were performed at two-day intervals, including the 8th day.

An overview of inflammatory bowel disease induction, intestinal organoid transplantation, and TNFα inhibitor administration is shown in FIG. 1, and the control group and experimental group are summarized in Table 1 below.

TABLE 1

|  | Intestinal organoids | TNFα inhibitor (anti-mouse TNFα antibody) |
|---|---|---|
| Normal control group | — | — |
| Negative control group (Vehicle) | — | — |
| Experimental group 1 | — | Single administration |
| Experimental group 2 | — | Five times administration |
| Experimental group 3 | Twice transplantation | — |
| Experimental group 4 | Twice transplantation | Single administration |

Thereafter, lesions of the intestinal mucosa and transplanted intestinal organoids were observed through colonoscopy at intervals of 1 to 2 weeks from the start date of the experiment.

Figure 2:
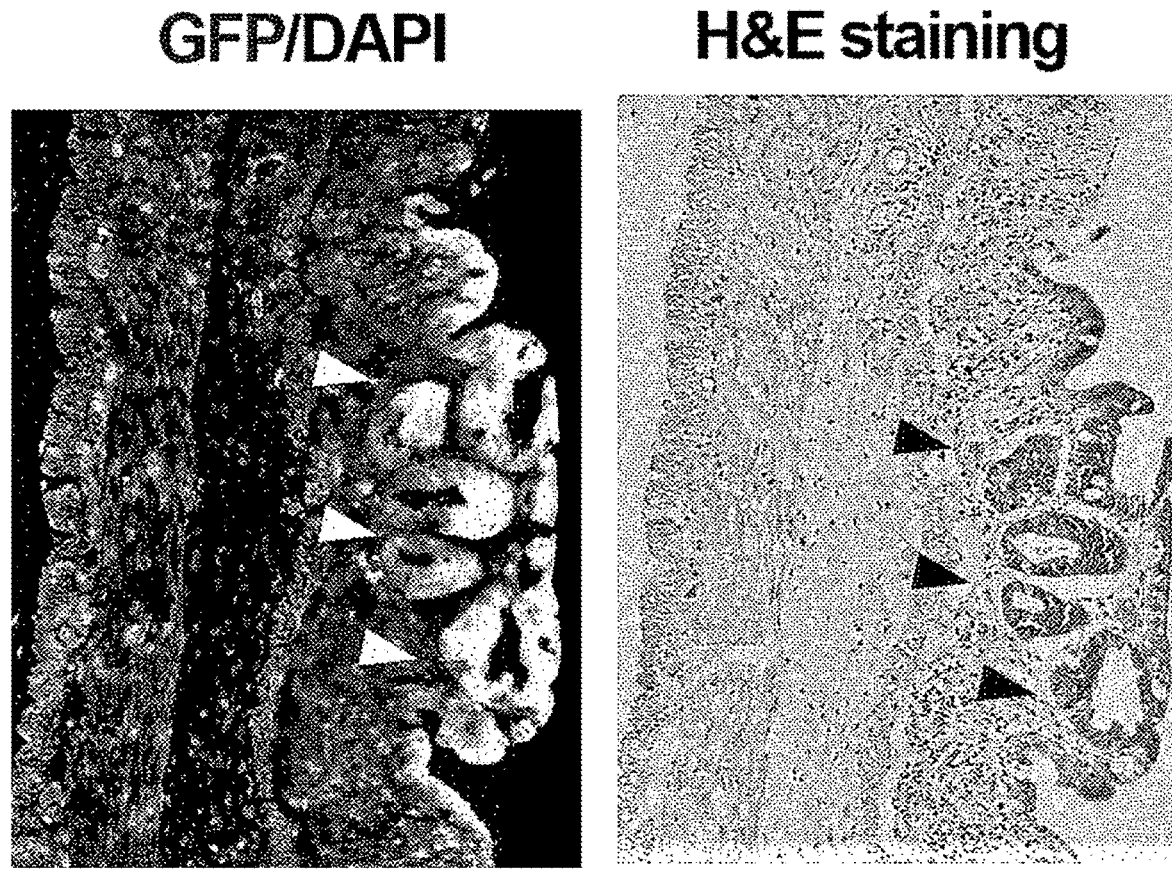
FIG. 2 is an image showing the results of H&E staining and GFP/DAPI analysis of intestinal tissue in which a combination of intestinal organoids and TNFα inhibitors are administrated.

As a result, as shown in FIG. 2, it was confirmed that the transplanted intestinal organoids were well engrafted in the intestinal tissue.

Example 1-2. Survival Rate

After transplanting the intestinal organoid and administering the TNFα inhibitor by the method according to Example 1-1, the survival rate of the subject was evaluated as a prevention or treatment effect of inflammatory bowel disease.

Specifically, the survival rate of the subject following the intestinal organoid transplantation and the TNFα inhibitor administration was calculated in the following formula for each group when the number of the subject decreased, and was evaluated using the Kaplan-Meier survival assay.

Survival rate of subject=number of survived animals/
total number of animals×100(%)

Figure 3:
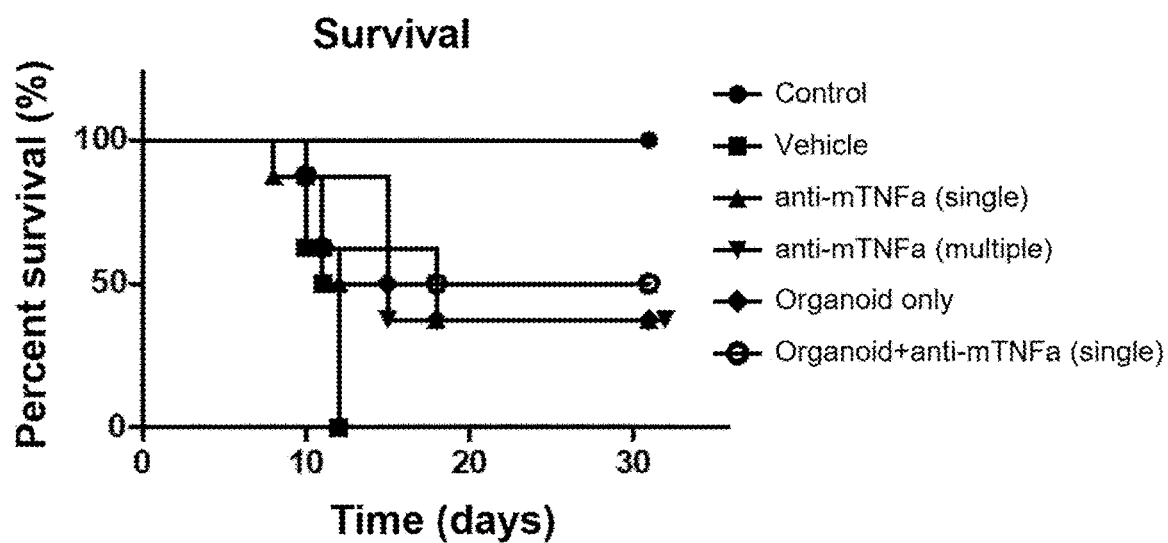
FIG. 3 is a graph showing the survival rate of subjects with inflammatory bowel disease, wherein the subject had single administration of a TNFα inhibitor, multiple administration of a TNFα inhibitor, transplantation of an intestinal organoid alone, or a combination of an intestinal organoid and a TNFα inhibitor.

As a result, FIG. 3 shows that in the negative control group suffering from inflammatory bowel disease, all the mice died on the 10th day after the start of the experiment.

In addition, in the case of Experimental Groups 1 and 2, in which only the TNFα inhibitor was administered single or multiple times, and Experimental Group 3, in which only the intestinal organoid was transplanted alone, the subjects started to die from the 10th day (2 or 3 days after the first single use). On the 15th day (7 or 8 days after the first single use), more than half of the subjects died, recording a survival rate of about 40%.

On the contrary, in the case of Experimental Group 4, in which the intestinal organoid and TNFα inhibitor were used in combination, the subjects started to die from the 10th day (2 days after the first combination), but the number of surviving subjects was higher than that of the subjects using the intestinal organoid or TNFα inhibitor alone. The survival rate of about 50% was recorded until the 18th day (10 days after the first combination), showing that the survival rate significantly increased by about 10% compared to the case of using the intestinal organoid or TNFα inhibitor alone.

That is, there was no difference in the survival rate between single administration and multiple administration of the TNFα inhibitor, and the effect of using an intestinal organoid in combination with a single administration of the TNFα inhibitor was significantly more than that of multiple administration of the TNFα inhibitor by about 10% or more.

From the results above, it was confirmed that the combination of intestinal organoids and TNFα inhibitors exhibited excellent synergistic effects in the prevention or treatment of inflammatory bowel disease.

Example 1-3. Body Weight

After transplanting the intestinal organoid and administering the TNFα inhibitor by the method according to Example 1-1, the body weight of the subject was evaluated as a prevention or treatment effect of inflammatory bowel disease.

Specifically, the change in body weight of mouse after administration of DSS and a therapeutic substance was observed daily. Assuming that the subject's body weight before the start of the test is 100%, the pattern of the decrease in body weight due to DSS-induced bowel disease and the increase in the body weight according to the treatment with a therapeutic substance was graphed. At the end of the test, one-way ANOVA was performed for the difference in body weight between each group using the GraphPad Prism ver.3 statistical program, and the significance of the treatment effect was confirmed by performing the Tukey post hoc test (* p-value<0.05).

Figure 4:
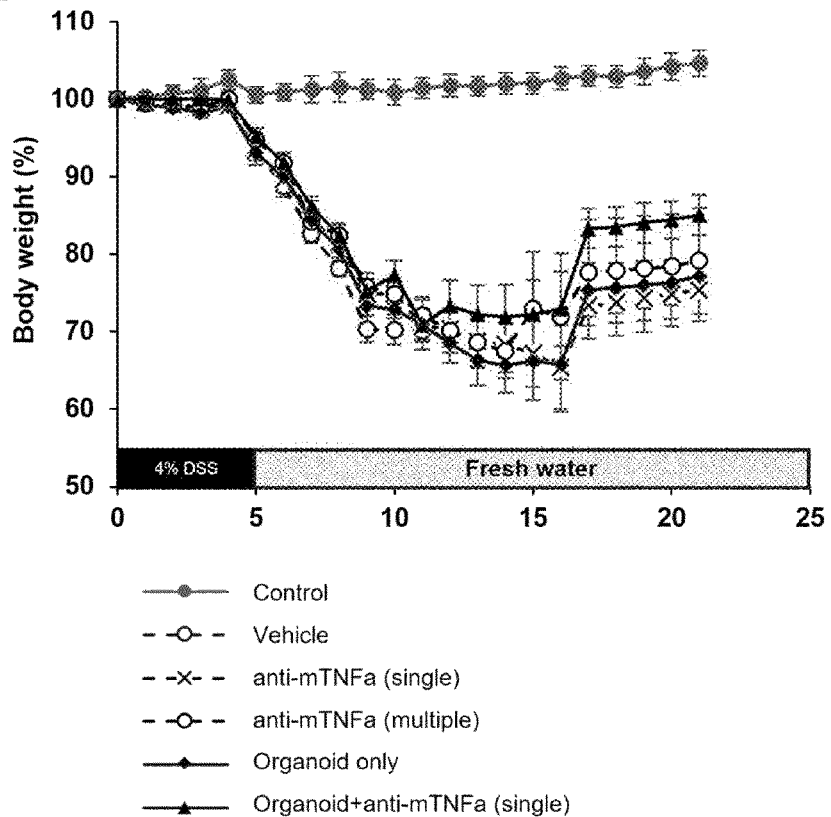
FIG. 4 is a graph showing the degree of weight gain or loss of subjects with inflammatory bowel disease, wherein the subject had single administration of a TNFα inhibitor, multiple administration of a TNFα inhibitor, single transplantation of an intestinal organoid, or a combination of an intestinal organoid and a TNFα inhibitor. A shows the increase/decrease rate of body weight, and B shows the final measured weight (g).
Figure 4:
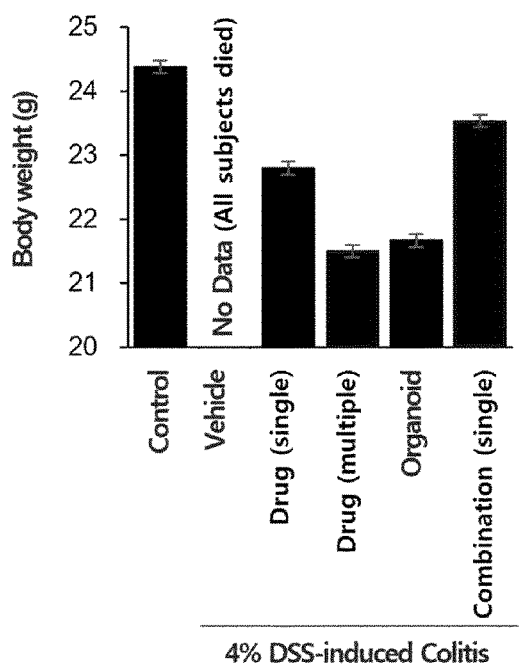

As a result, as shown in A and B of FIG. 4, the negative control group suffering from inflammatory bowel disease lost about 30% in body weight compared to the normal control group on the 10th day after the start of the experiment, and after that, all subjects died.

In addition, in the case of Experimental Groups 1 and 2, in which only the TNFα inhibitor was administered single or multiple times, and Experimental Group 3, in which only the intestinal organoid was transplanted alone, the body weight decreased by about 30-40% compared to the normal control group until the 15th day of the experiment (7 days or 8 days after the first single use). After that, the body weight increased slightly, and on the 23rd day of the experiment (15 days or 16 days after the first single use), the weight loss rate was about 20 to 25% compared to the normal control group.

Specifically, on the 23rd day of the experiment (15 days or 16 days after the first single use), compared to the normal control group, the weight loss rate was about 20% in Experimental Group 1 (single administration of TNFα inhibitor alone), 25% in Experimental Group 2 (multiple administration of TNFα inhibitor alone), and 22% in Experimental Group 3 (transplantation of intestinal organoids alone).

On the contrary, in the case of experimental group 4 in which the intestinal organoid and TNFα inhibitor were used in combination, the body weight decreased by about 25% compared to the normal control group by the 10th day (2 days after the first combination). After that, the body weight increased significantly, and on the 23rd day of the experiment (15 days after the first combination), the weight decreased by about 15% compared to the normal control group. In addition, it was confirmed that the survival rate was significantly increased by about 10% compared to the case of using drug alone.

Through the above results, it was confirmed that the combination of intestinal organoids and TNFα inhibitors exhibited excellent synergistic effects for the prevention or treatment of inflammatory bowel disease, and the combination use has a better therapeutic effect than multiple administration of the TNFα inhibitor.

Example 1-4. DAI (Disease Activity Index)

After transplanting the intestinal organoid and administering the TNFα inhibitor by the method according to Example 1-1, a reduction effect on the disease activity index (DAI) of the subject was confirmed as prevention or treatment effect of inflammatory bowel disease.

Specifically, DAI was analyzed for parameters consisting of weight loss, stool consistency, and fractional occult blood. After observing the symptoms for each parameter, they were scored according to the degree of change, and by summing them up. After that, the symptoms were classified as follows: DAI of 0 to 1 is normal, DAI of 2 to 4 is mild, DAI of 5 to 7 is severe, and DAI of 8 to 10 is critical.

TABLE 2

| Parameters | Change | Score |
|---|---|---|
| Weight loss | 0 | 0 |
|  | 1 ≤ 5 Weight % | 1 |
|  | 5 ≤ 10 Weight % | 2 |
|  | 10 ≤ 20 Weight % | 3 |
|  | >20 Weight % | 4 |
| Stool consistency | negative | 0 |
|  | wet | 1 |
|  | soft | 2 |
|  | diarrhea | 3 |
| Fecal occult blood | normal | 0 |
|  | bloody stool | 1 |
|  | blood around the anus | 2 |
|  | gross bleeding | 3 |

Figure 5:
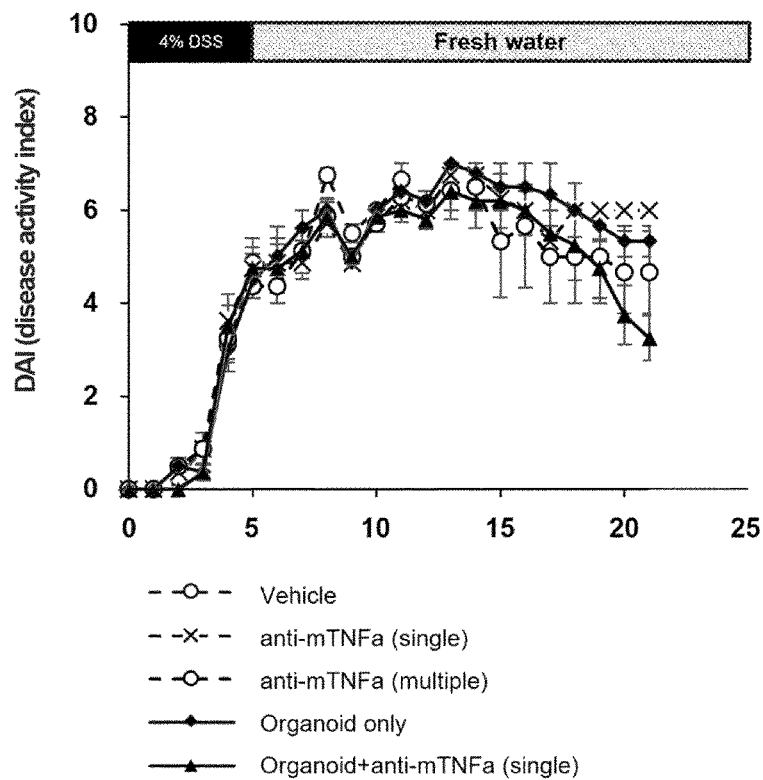
FIG. 5 is a graph showing the degree of DAI (disease activity index) increase or decrease of subjects with inflammatory bowel disease, wherein the subject had single administration of a TNFα inhibitor, multiple administration of a TNFα inhibitor, single transplantation of an intestinal organoid, or a combination of an intestinal organoid and a TNFα inhibitor. A shows the increase/decrease ratio of DAI, and B shows the final scored DAI.
Figure 5:
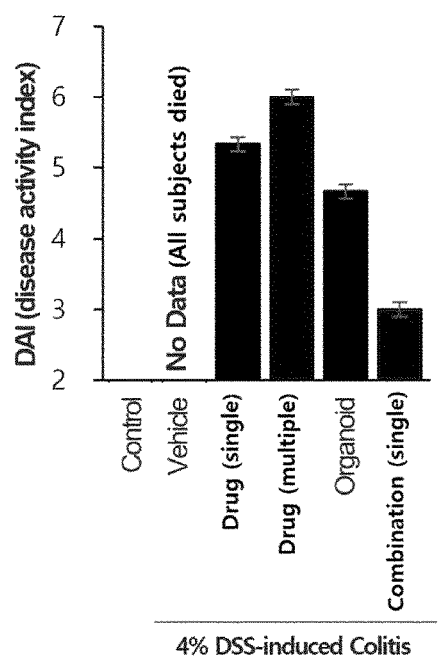

As a result, as shown in A and B of FIG. 5, the negative control group not administering the intestinal organoid nor the TNFα inhibitor showed severe inflammatory bowel disease symptoms in which the DAI increased to about 6 compared to the normal control group on the 10th day of the experiment, and after that, all subjects died. In addition, in the case of Experimental Groups 1 and 2, in which only the TNFα inhibitor was administered single or multiple times, and Experimental Group 3, in which only the intestinal organoid was transplanted alone, the DAI increased to about 6 to 7 which showed severe inflammatory bowel disease symptoms until the 15th day of the experiment (7 days or 8 days after the first single use). The DAI decreased slightly to about 5 to 6 on the 23rd day of the experiment (15 days or 16 days after the first single use), but the inflammatory bowel disease symptoms were still severe. Specifically, on the 23rd day of the experiment (15 days or 16 days after the first single use), compared to the normal control group, the DAI was about 5.5 in Experimental Group 1 (single administration of TNFα inhibitor alone), 6 in Experimental Group 2 (multiple administration of TNFα inhibitor alone), and 5 in Experimental Group 3 (transplantation of intestinal organoids alone).

On the contrary, in the case of Experimental Group 4 in which the intestinal organoid and TNFα inhibitor were used in combination, the DAI increased to about 6 which showed severe inflammatory bowel disease symptoms by the 13th day (5 days after the first combination). After that, the DAI decreased to about 3 which showed mild inflammatory bowel disease symptoms on the 23rd day of the experiment (15 days after the first combination). It was confirmed that the DAI was significantly decreased by about 2 to 3 compared to the case of using drug alone, which means that the symptoms relieved from severe to mild.

That is, with respect to the DAI, the effect of multiple administration of the TNFα inhibitor is better than that of the single administration of the TNFα inhibitor. However, the combination use of an intestinal organoid and the TNFα inhibitor (single administration) showed remarkably better effect of reducing DAI by 2 to 3 than the multiple administration of the TNFα inhibitor.

In particular, in the case of Experimental Group 4 of the combination, the DAI decreases sharply from the 13th day (after 5 days of the first combination) of the start of the experiment. Considering that in the case of Experimental Groups 1 to 3 of single use, DAI decreased from the 15th day (7 days or 8 days after the first single use) from the start of the experiment, it was confirmed that the combination use of intestinal organoids and TNFα inhibitor showed the therapeutic effect of inflammatory bowel disease in a shorter time.

Through the above results, it was confirmed that the combination of intestinal organoids and TNFα inhibitors exhibited excellent synergistic effects for the prevention or treatment of inflammatory bowel disease with the symptoms including weight loss, stool consistency and fecal occult blood, etc., and the combination use has a better therapeutic effect than the multiple administration of the TNFα inhibitor.

Example 2. Effect on TNBS-Induced Inflammatory Bowel Disease

Example 2-1. Combination and Transplantation

Intestinal organoids were transplanted into an inflammatory bowel disease mouse model and an anti-inflammatory agent was administered to confirm the prevention or treatment efficacy of inflammatory bowel disease by the combination of the intestinal organoid and anti-inflammatory agent.

Specifically, the inflammatory bowel disease mouse model was prepared in the follows. 1 w/v % TNBS (trinitrobenzene sulfonic acid) presensitization solution was applied to the dorsal skin of C57BL/6 mice (male, 10 weeks, average body weight 24 g), and then only mice that did not lose weight nor show other specific symptoms for 8 days thereafter were selected and used. Then, 2.5 w/v % TNBS mixed in ethanol solution was intrarectally administered to the mice. It is known that when TNBS is mixed with an ethanol solution and intrarectally administered, a disease similar to inflammatory bowel disease in human is induced. Ethanol plays a major role in the break of the intestinal mucosal epithelial barrier and the entry of TNBS into the intestinal wall, and TNBS causes acute necrosis through oxidative damage.

The day after TNBS rectal administration, 100 ag of anti-mouse TNFα antibody (BioLegend) as a TNFα inhibitor was intraperitoneally injected. In addition, on the day after administration of the TNFα inhibitor, GFP-expressing mouse intestinal organoids was transplanted at a number of $1\times10^6$ cells/animal into the intestine. Transplantation was carried out by an endoscopic transplantation method, and fibrin glue was used as a scaffold for intestinal organoids. Meanwhile, in the case of combinational administration of a TNFα inhibitor and intestinal organoids, 100 ag of an anti-mouse TNFα antibody and $1\times10^6$ cells/animal of intestinal organoids were simultaneously administered and transplanted on the day after TNBS rectal administration.

Figure 6:
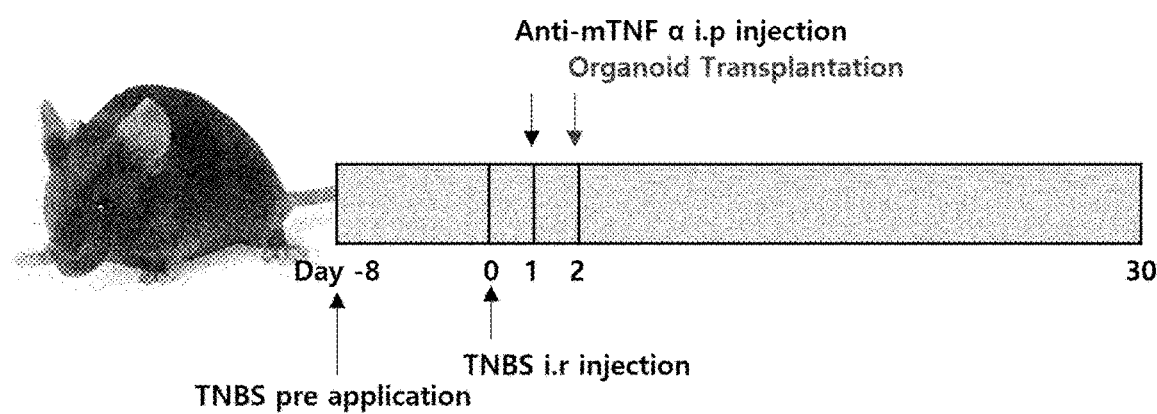
FIG. 6 is a schematic diagram of a method for inducing inflammatory bowel disease using TNBS, transplanting an intestinal organoid and administering a TNFα inhibitor.

An overview of inflammatory bowel disease induction, intestinal organoid transplantation, and TNFα inhibitor administration is shown in FIG. 6, and the control group and experimental group are summarized in Table 3 below.

TABLE 3

| | Scaffold | Administration/transplantation formulation |
|---|---|---|
| Control | — | — |
| Negative control (vehicle) | Fibrin glue | — |
| Experimental group 5 | Fibrin glue | 100 μg of anti-mouse TNFα antibody |
| Experimental group 6 | Fibrin glue | intestinal organoids ($1 \times 10^6$ cells/animal) |
| Experimental group 7 | Fibrin glue | 100 μg of anti-mouse TNFα; and intestinal organoids ($1 \times 10^6$ cells/animal) |

Thereafter, lesions of the intestinal mucosa and transplanted intestinal organoids were observed through colonoscopy at intervals of 1 to 2 weeks from the start date of the experiment.

Figure 7:
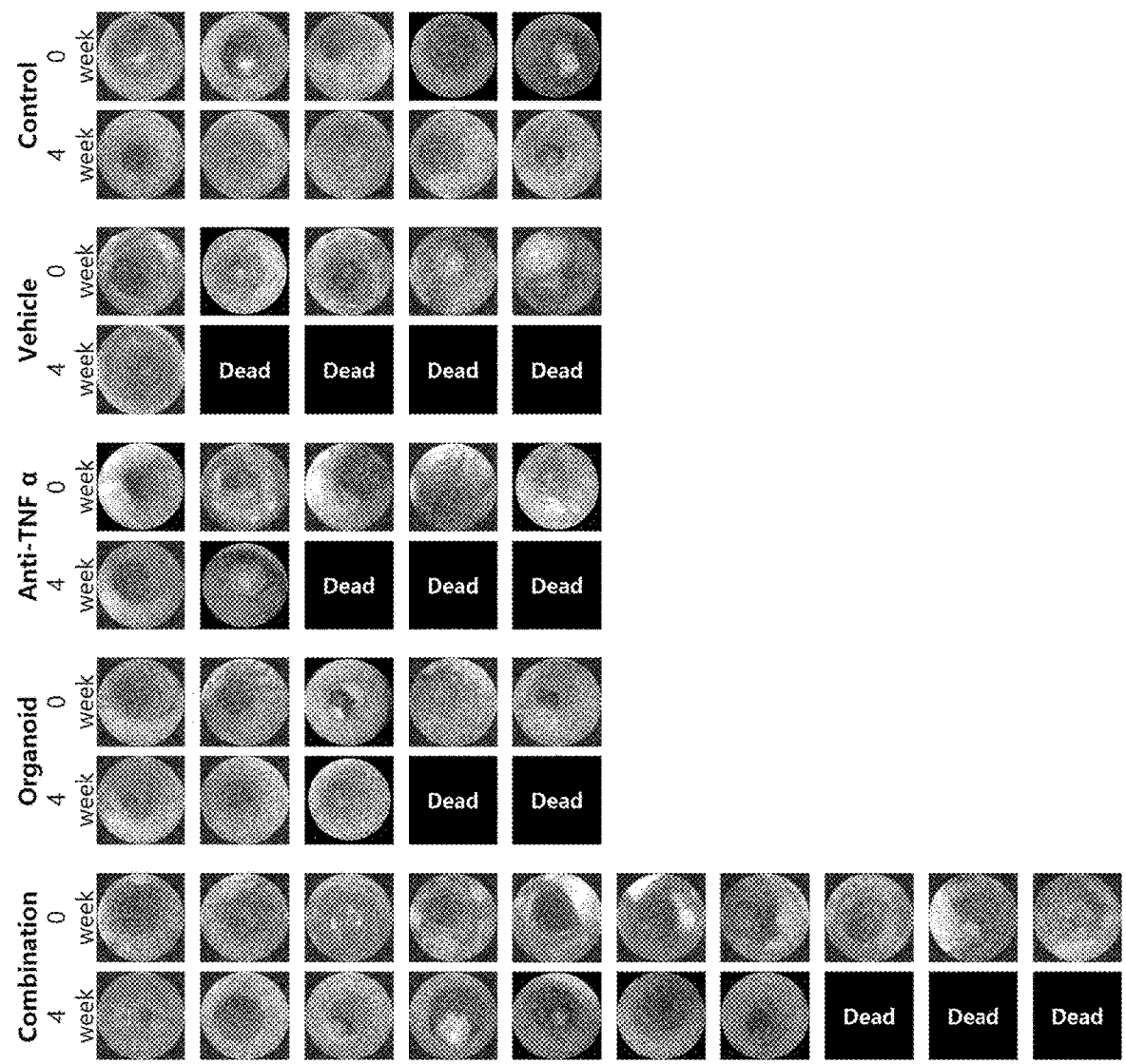
FIG. 7 is an image showing intestinal tissue in a subject with inflammatory bowel disease, wherein the subject had administration of a TNFα inhibitor alone, transplantation of an intestinal organoid alone, or a combination of an intestinal organoid and a TNFα inhibitor.

As a result, as shown in FIG. 7, the vehicle group showed severe inflammatory and ulcerative lesions (white parts) immediately after the occurrence of inflammatory bowel disease induced by TNBS, and most of the subjects died at the 4th week of occurrence. It was confirmed that the prepared animal model had severe inflammatory bowel disease.

In addition, in the case of Experimental Group 5, in which only the TNFα inhibitor was administered alone, the survival rate increased compared to the vehicle group at the 4th week of occurrence. However, it was observed that many subjects died, and some inflammatory and ulcerative lesions still remained in the surviving subjects. Also, in the case of Experimental Group 6, in which only intestinal organoids were transplanted, it was confirmed that some inflammatory and ulcerative lesions still remained in the subjects survived until the 4th week of occurrence.

On the contrary, in the case of Experimental Group 7 in which the intestinal organoid and TNFα inhibitor were used in combination, inflammatory and ulcerative lesions were observed similar to those of the vehicle group immediately after the start of the experiment. However, inflammatory and ulcerative lesions almost disappeared in the survived subjects up to the 4th week of occurrence, and it was observed that the bumpy intestinal surface seen in some photos is part of the process that appears as the inflammation or ulcer is treated.

Through the above results, it was confirmed that the combination of intestinal organoids and TNFα inhibitors exhibited excellent synergistic effects for the prevention or treatment of inflammatory bowel disease.

Example 2-2. Survival Rate

After transplanting the intestinal organoid and administering the TNFα inhibitor by the method according to Example 2-1, the survival rate of the subject was evaluated as a prevention or treatment effect of inflammatory bowel disease.

Specifically, the survival rate of the subject following intestinal organoid transplantation and TNFα inhibitor administration was calculated in the following formula for each group when the number of the subject decreased, and was evaluated using the Kaplan-Meier survival assay.

Survival rate of subject=number of survived animals/total number of animals×100(%)

Figure 8:
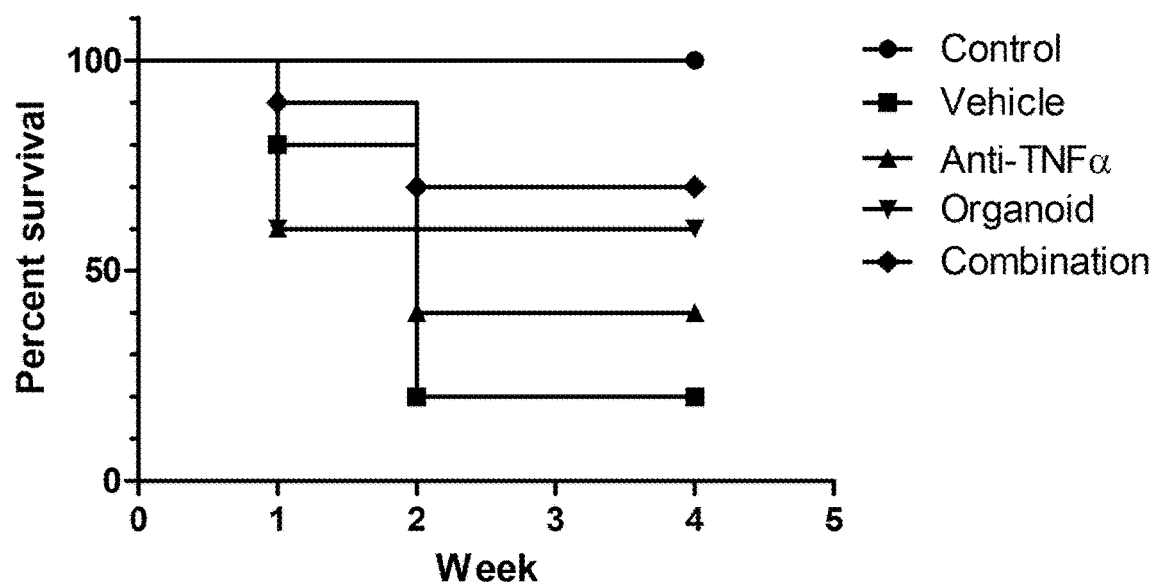
FIG. 8 is a graph showing the survival rate of subjects with inflammatory bowel disease, wherein the subject had administration of a TNFα inhibitor alone, transplantation of an intestinal organoid alone, or a combination of an intestinal organoid and a TNFα inhibitor.

As a result, in the vehicle group suffering from inflammatory bowel disease as shown in FIG. 8, most of the subjects died on the second week of the experiment, and the survival rate was only about 20%.

In addition, in the case of Experimental Group 5, in which only the TNFα inhibitor was administered alone, the subject started to die from the first week of the experiment, and more than half of the subjects died at the second week, which recorded a survival rate of about 40%. Even in the case of Experimental Group 6, in which only intestinal organoids were transplanted, the subject started to die from the first week of the experiment, and a survival rate of about 60% was recorded at the end of the experiment.

On the contrary, in the case of Experimental Group 7 in which the intestinal organoid and TNFα inhibitor were used in combination, a high survival rate of about 90% was shown at the first week of the experiment, and a survival rate of about 70% was recorded at the end of the experiment. It was confirmed that the survival rate was significantly increased by about 10% compared to the case of using drug alone.

Through the above results, it was confirmed that the combination of intestinal organoids and TNFα inhibitors exhibited excellent synergistic effects for the prevention or treatment of inflammatory bowel disease.

Example 2-3. Body Weight

After transplanting the intestinal organoid and administering the TNFα inhibitor by the method according to Example 2-1, the body weight of the subject was evaluated as a prevention or treatment effect of inflammatory bowel disease.

Assuming that the subject's body weight before the start of the test is 100%, the pattern of the decrease in body weight due to TNBS-induced bowel disease and the increase in the body weight according to the treatment with a therapeutic substance was graphed. At the end of the test, one-way ANOVA was performed for the difference in body weight between each group using the GraphPad Prism ver.3 statistical program, and the significance of the treatment effect was confirmed by performing the Tukey post hoc test (* p-value<0.05).

Figure 9:
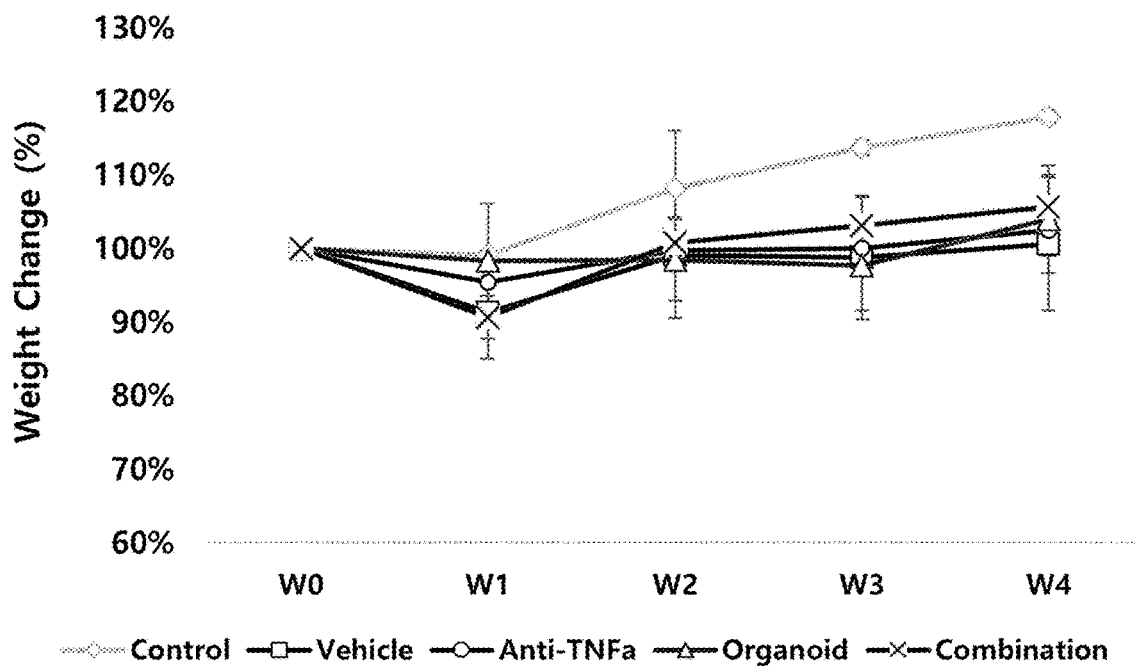
FIG. 9 is a graph showing the degree of weight gain or loss of subjects with inflammatory bowel disease, wherein the subject had administration of a TNFα inhibitor alone, transplantation of an intestinal organoid alone, or a combination of an intestinal organoid and a TNFα inhibitor.

As a result, as shown in FIG. 9, Experimental Group 7 in which the intestinal organoid and TNFα inhibitor were used in combination showed a similar body weight to the Experimental Group 5 in which only the TNFα inhibitor was administered, or the Experimental Group 6 in which only the intestinal organoid was transplanted.

Through the above results, it was confirmed that the combination of intestinal organoids and TNFα inhibitors are safely used for the prevention or treatment of inflammatory bowel disease because they do not exhibit toxicity, such as a significant loss in body weight.

Example 2-4. UCEIS (Ulcerative Colitis Endoscopic Index of Severity)

After transplanting the intestinal organoid and administering the TNFα inhibitor by the method according to Example 2-1, a reduction level on modified Ulcerative Colitis Endoscopic Index of Severity (UCEIS) in the subject was confirmed as prevention or treatment effect of ulcerative colitis.

Specifically, modified UCEIS was analyzed for parameters consisting of Vascular Pattern, Bleeding, Ulcers, and Survival. After observing the symptoms for each parameter, they were scored according to the degree of change. By summing them up, the symptoms was classified as follows: UCEIS of 0 to 1 is normal, UCEIS of 2 to 4 is mild, UCEIS of 5 to 6 is severe, and UCEIS of 7 to 8 is critical.

TABLE 4

| Parameters | Change | Score |
| --- | --- | --- |
| Vascular Pattern | normal | 0 |
|  | Patchy Obliteration | 1 |
|  | Obliterated | 2 |
| Bleeding | none | 0 |
|  | mucosal | 1 |
|  | luminal mild | 2 |
|  | luminal moderate or severe | 3 |
| Ulcers | none | 0 |
|  | Erosions | 1 |
|  | Superficial ulcer | 2 |
|  | Deep ulcer | 3 |
| Survival | survival | 0 |
|  | dead | 8 |

Figure 10:
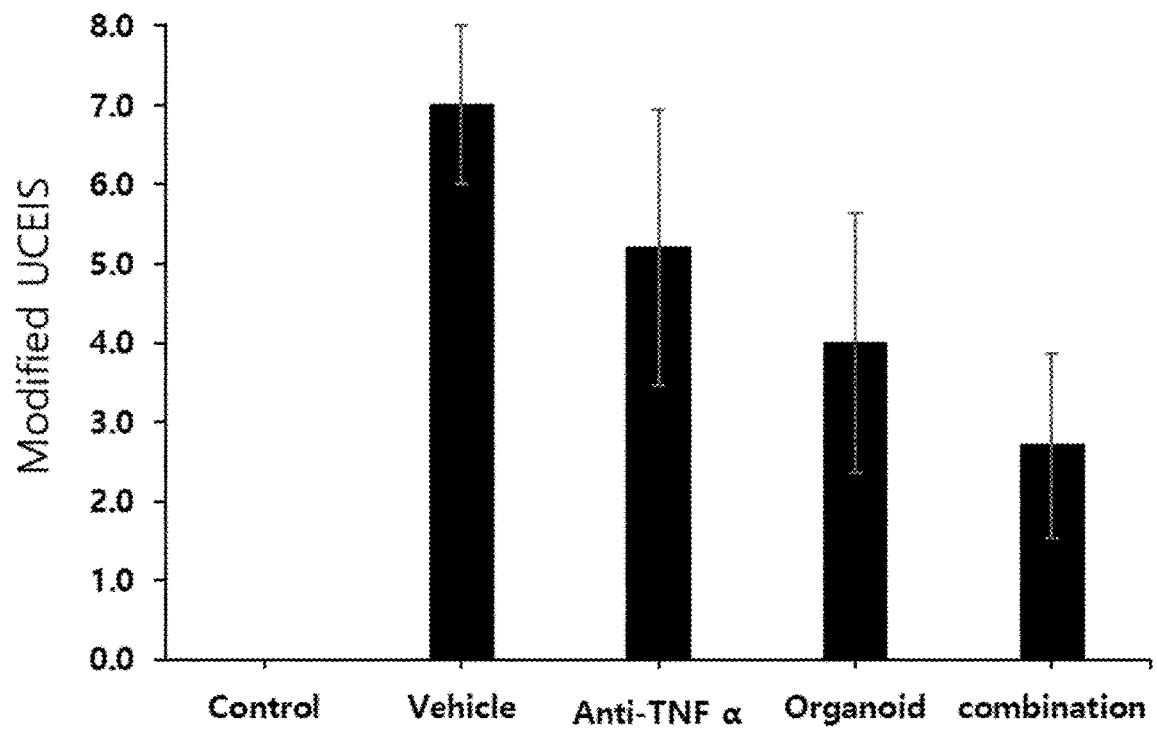
FIG. 10 is a graph showing the degree of modified UCEIS (Ulcerative Colitis Endoscopic Index of Severity) in subjects with ulcerative colitis, wherein the subject had administration of a TNFα inhibitor alone, transplantation of an intestinal organoid alone, or a combination of an intestinal organoid and a TNFα inhibitor.

As a result, as shown in FIG. 10, the vehicle group not administrating the intestinal organoid nor the TNFα inhibitor showed critical ulcerative colitis symptoms in which the modified UCEIS increased to about 8. In addition, in the case of Experimental Group 5 in which only the TNFα inhibitor was administered alone, the modified UCEIS showed severe ulcerative colitis symptoms that increased to about 5 to 6, and Experimental Group 6 in which only intestinal organoids were administered alone showed severe ulcerative colitis symptoms that the modified UCEIS increased up to about 5.

On the contrary, in the case of Experimental Group 7 in which the intestinal organoid and TNFα inhibitor were used in combination, the modified UCEIS reduced up to about 3 and it showed only mild symptoms of ulcerative colitis.

Through the above results, it was confirmed that the combination of intestinal organoids and TNFα inhibitors exhibited excellent synergistic effects for the prevention or treatment of inflammatory bowel disease such as ulcerative colitis, and the combination use can significantly alleviate symptoms from severe to mild.

Example 2-5. DAI (Disease Activity Index)

After transplanting the intestinal organoid and administering the TNFα inhibitor by the method according to Example 2-1, a reduction level on the disease activity index (DAI) of the subject was confirmed as prevention or treatment effect of inflammatory bowel disease. Specifically, DAI was analyzed in the same manner as in Example 1-4.

Figure 11:
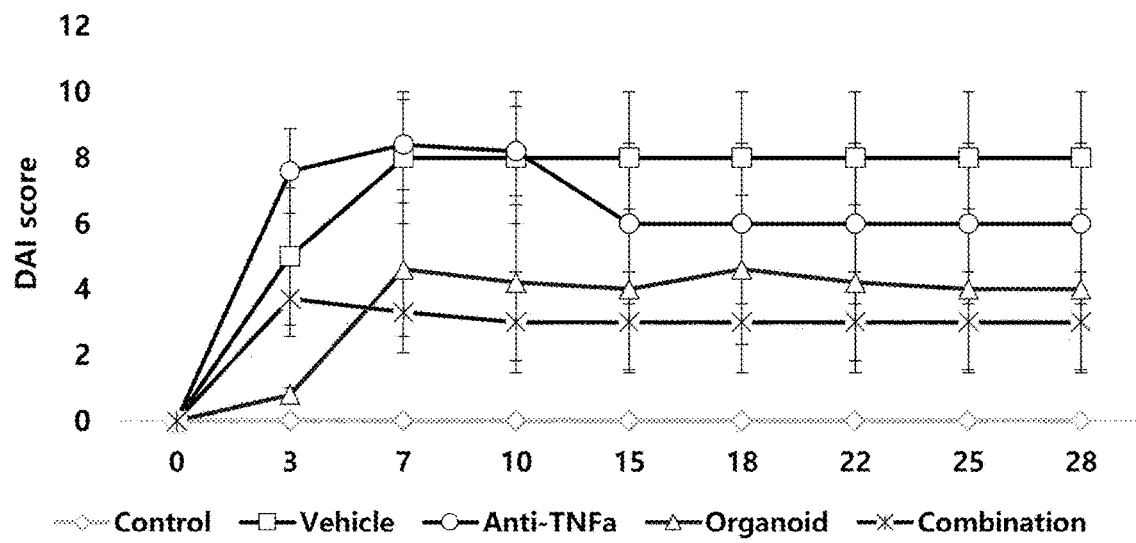
FIG. 11 is a graph showing the degree of DAI (disease activity index) increase or decrease in subjects with inflammatory bowel disease, wherein the subject had administration of a TNFα inhibitor alone, transplantation of an intestinal organoid alone, or a combination of an intestinal organoid and a TNFα inhibitor.

As a result, as shown in FIG. 11, the vehicle group not administrating the intestinal organoid nor the TNFα inhibitor showed critical inflammatory bowel disease symptoms in which the DAI increased to about 8 compared to the normal control group on the 10th day of the experiment.

In addition, in the case of Experimental Group 5 in which only the TNFα inhibitor was administered alone, the DAI showed severe inflammatory bowel disease symptoms that increased to about 6 to 7, and Experimental Group 6 in which only intestinal organoids were administered alone showed severe inflammatory bowel disease symptoms whose the DAI increased up to about 5.

On the contrary, in the case of Experimental Group 7 in which the intestinal organoid and TNFα inhibitor were used in combination, the DAI reduced up to about 3 and it showed only mild symptoms of inflammatory bowel disease. The symptoms did not worsen and remained until the end of the experiment.

Through the above results, it was confirmed that the combination of intestinal organoids and TNFα inhibitors exhibited excellent synergistic effects for the prevention or treatment of inflammatory bowel disease, and the combination use can significantly alleviate symptoms from severe to mild.

Example 2-6. Intestinal Mucosa Regeneration

Intestinal organoid and TNFα inhibitor were transplanted and administered by the method according to Example 2-1, and the effect of promoting intestinal mucosa regeneration in the subject was evaluated as a prevention or treatment effect of inflammatory bowel disease. Specifically, the degree of regeneration of the intestinal mucosa was confirmed by analyzing intestinal organoids engrafted in the intestinal tissue and the structures of intestinal tissue.

Figure 12:
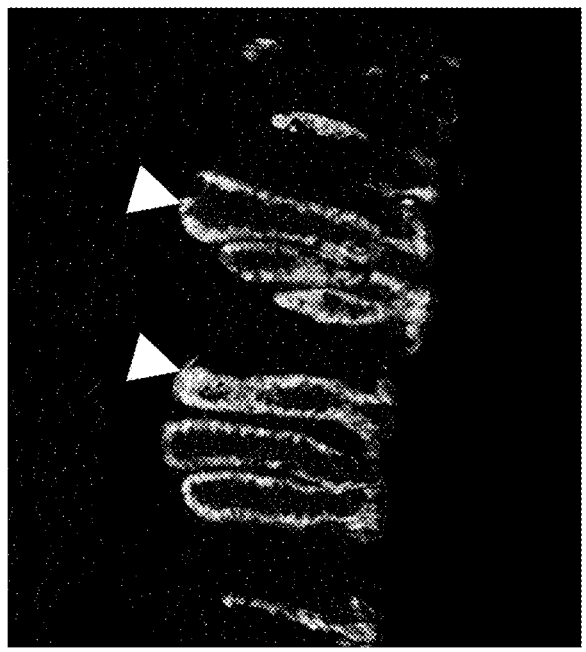
FIG. 12 is an image showing the results of H&E staining and GFP/DAPI analysis of intestinal tissue in which a combination of intestinal organoids and TNFα inhibitors are used.
Figure 12:

As a result, in Experimental Group 7, in which the intestinal organoid and TNFα inhibitor were used in combination, as shown in FIG. 12, it was confirmed that intestinal organoids were engrafted in the intestinal mucosa and formed normal tissues by replacing damaged tissues.

Through the above results, it was confirmed that the combination of intestinal organoids and TNFα inhibitors exhibited effects for the prevention or treatment of inflammatory bowel disease including the symptoms such as weight loss, diarrhea, and bloody stool by restoring tissue damaged due to inflammation.

Example 2-7. Intestinal Mucosa Fibrosis

Intestinal organoid and TNFα inhibitor were transplanted and administered by the method according to Example 2-1, and the effect of inhibiting intestinal mucosa fibrosis in the subject was evaluated as a prevention or treatment effect of inflammatory bowel disease.

Specifically, the degree of progression of fibrosis of the intestinal mucosa due to inflammation and the degree of inhibition of fibrosis of the intestinal mucosa by the intestinal organoid and/or TNFα inhibitor were evaluated by measuring the length of the intestine. In the case of subjects suffering from inflammatory bowel disease, the intestinal mucosa is subject to fibrosis due to inflammation, and as a result, the length of the intestine is shortened and hardened. Fibrosis causes abnormal changes in the intestinal tissue and interferes with the intake of nutrients, which is a factor that hinders the cure of diseases.

Specifically, the change in intestinal length to determine the difference in intestinal fibrosis according to TNBS administration and treatment of drugs was observed by measuring the length from the cecum to the anus by autopsying the mice at the end of the test. The difference in bowel length between each group was confirmed by one-way ANOVA using the GraphPad Prism ver.3 statistical program, and the significance of the therapeutic effect on the inhibition of intestinal fibrosis was confirmed by performing the Tukey post-hoc test (*p-value<0.05).

Figure 13:
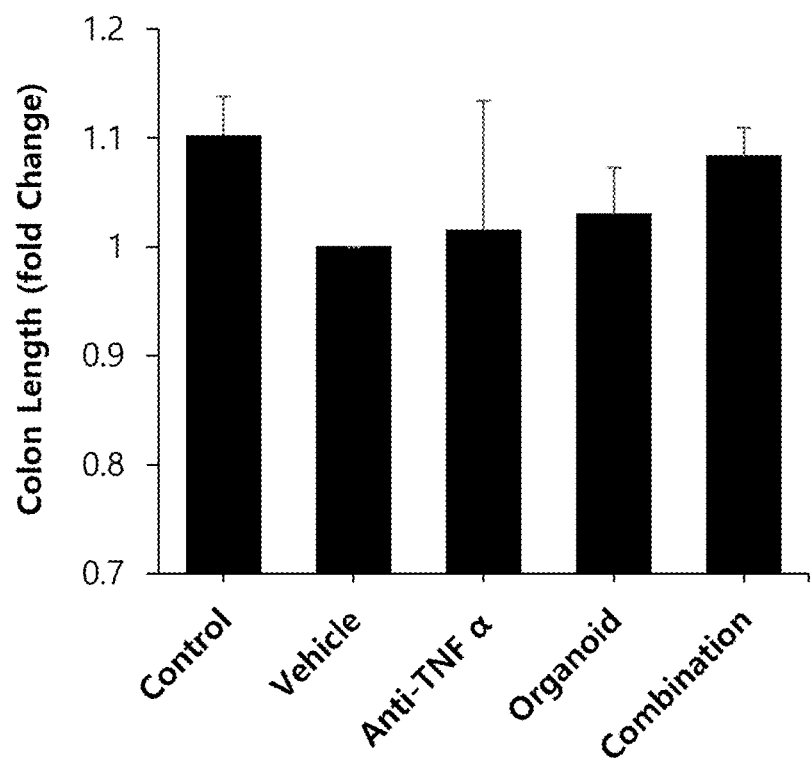
FIG. 13 is a graph showing the degree of intestinal length increase or decrease in subjects with inflammatory bowel disease, wherein the subject had administration of a TNFα inhibitor alone, transplantation of an intestinal organoid alone, or a combination of an intestinal organoid and a TNFα inhibitor.
Figure 14:
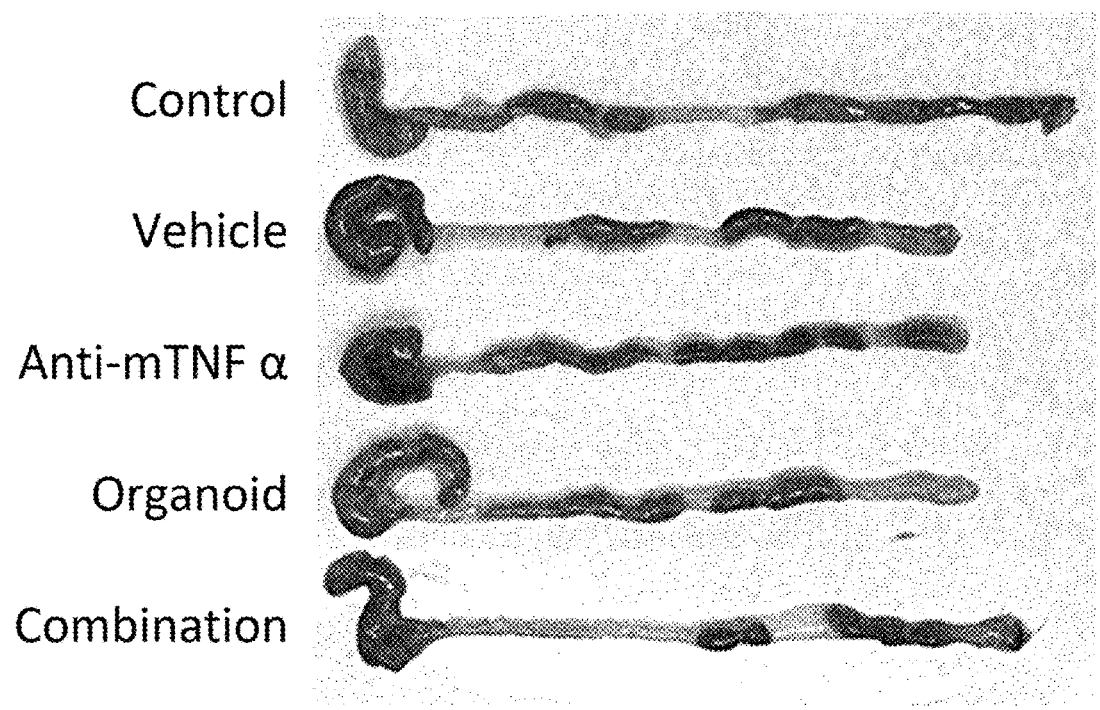
FIG. 14 is an image showing the degree of intestinal length increase or decrease in subjects with inflammatory bowel disease, wherein the subject had administration of a TNFα inhibitor alone, transplantation of an intestinal organoid alone, or a combination of an intestinal organoid and a TNFα inhibitor.

As a result, as shown in FIGS. 13 and 14, in Experimental Group 5 (the TNFα inhibitor was administered alone) and Experimental Group 6 (the intestinal organoid was transplanted alone), fibrosis due to inflammation progressed. As a result, the length of the large intestine was shortened, which was similar to that of the vehicle group.

On the contrary, in Experimental Group 7 in which the intestinal organoid and TNFα inhibitor were used in combination, it was confirmed that inflammation-induced fibrosis of the intestinal mucosa was suppressed. Accordingly, the length of the large intestine was not shortened, which was similar to that of the normal control group.

Through the above results, it was confirmed that the combination of intestinal organoids and TNFα inhibitors exhibited effects for the prevention or treatment of inflammatory bowel disease including the symptoms of decreased body weight, diarrhea, and bloody stool by inhibiting or alleviating the progression of fibrosis in the inflamed area.

What is claimed is:

1. A pharmaceutical composition for preventing or treating inflammatory bowel disease, comprising an intestinal organoid and a TNFα inhibitor,
    wherein the inflammatory bowel disease is one or more selected from the group consisting of ischemic colitis, intestinal Behcet's disease, Crohn's disease, ulcerative colitis and ulcerative proctitis.

2. The pharmaceutical composition according to claim 1, wherein the TNFα inhibitor is a compound, a peptide, a peptide mimetic, a fusion protein, an antibody, an aptamer, or antibody drug conjugate (ADC) that binds specifically to TNFα protein.

3. The pharmaceutical composition according to claim 1, wherein the TNFα inhibitor is an antisense nucleic acid, a siRNA, a shRNA, a miRNA or a ribozyme that binds in a complementary manner to a DNA or a mRNA of TNFα.

4. The pharmaceutical composition according to claim 1, wherein the composition decreases Disease Activity Index (DAI).

5. The pharmaceutical composition according to claim 1, wherein the composition improves or ameliorates one or more symptoms selected from the group consisting of weight loss, stool consistency and fecal occult blood in a subject.

6. The pharmaceutical composition according to claim 1, wherein the composition inhibits or ameliorates fibrosis caused by inflammation.

7. The pharmaceutical composition according to claim 1, wherein the intestinal organoid and the TNFα inhibitor are administered simultaneously, sequentially, or individually to a subject.

* * * * *